US008668688B2

(12) United States Patent
Rusin

(10) Patent No.: US 8,668,688 B2
(45) Date of Patent: Mar. 11, 2014

(54) SOFT TISSUE RF TRANSECTION AND RESECTION DEVICE

(75) Inventor: Chris Rusin, Golden, CO (US)

(73) Assignee: Covidien AG (CH)

( * ) Notice: Subject to any disclaimer, the term of this patent is extended or adjusted under 35 U.S.C. 154(b) by 0 days.

(21) Appl. No.: 13/551,005

(22) Filed: Jul. 17, 2012

(65) Prior Publication Data
US 2013/0030429 A1 Jan. 31, 2013

Related U.S. Application Data

(63) Continuation of application No. 11/418,879, filed on May 5, 2006, now abandoned.

(51) Int. Cl.
A61B 18/18 (2006.01)
(52) U.S. Cl.
USPC .................................. 606/48; 606/45
(58) Field of Classification Search
USPC .................... 606/32, 39, 41, 45, 48
See application file for complete search history.

(56) References Cited

U.S. PATENT DOCUMENTS

| | | |
|---|---|---|
| 2,031,682 A | 2/1936 | Frederick et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |

(Continued)

FOREIGN PATENT DOCUMENTS

| | | |
|---|---|---|
| DE | 2407559 | 2/1974 |
| DE | 24 29 021 A1 | 1/1976 |

(Continued)

OTHER PUBLICATIONS

International Search Report from Application No. EP 06 00 6908 dated Feb. 25, 2009.

(Continued)

Primary Examiner — Linda Dvorak
Assistant Examiner — Jaymi Della

(57) ABSTRACT

A method for performing an electrosurgical procedure is presented including providing an electrosurgical system having an electrosurgical generator, a first electrosurgical device including a first electrically conductive element, a second electrosurgical device including a second electrically conductive element configured to be coupled to a first location of a target tissue and a third electrosurgical device including a third electrically conductive element configured to be coupled to a second location of the target tissue. The method also includes the steps of positioning the second and third electrically conductive elements relative to one another, orienting and defining a direction and a length of a single resection line between the second and third electrically conductive elements, and moving the first electrically conductive element along the single resection line to desiccate or divide the target tissue.

17 Claims, 2 Drawing Sheets

(56) References Cited

U.S. PATENT DOCUMENTS

| | | | |
|---|---|---|---|
| 3,902,494 A | 9/1975 | Haberlen et al. | |
| 3,906,955 A | 9/1975 | Roberts | |
| 3,911,241 A | 10/1975 | Jarrard | |
| 3,967,084 A | 6/1976 | Pounds | |
| 3,974,833 A | 8/1976 | Durden, III | |
| 4,014,343 A | 3/1977 | Esty | |
| 4,032,738 A | 6/1977 | Esty et al. | |
| 4,034,761 A | 7/1977 | Prater et al. | |
| 4,038,984 A | 8/1977 | Sittner | |
| 4,074,718 A | 2/1978 | Morrison, Jr. | |
| 4,112,950 A | 9/1978 | Pike | |
| D253,247 S | 10/1979 | Gill | |
| 4,232,676 A | 11/1980 | Herczog | |
| 4,314,559 A | 2/1982 | Allen | |
| 4,375,220 A | 3/1983 | Matvias | |
| 4,411,266 A | 10/1983 | Cosman | |
| 4,427,006 A | 1/1984 | Nottke | |
| 4,443,935 A | 4/1984 | Zamba et al. | |
| 4,459,443 A | 7/1984 | Lewandowski | |
| 4,463,234 A | 7/1984 | Bennewitz | |
| 4,463,759 A | 8/1984 | Garito et al. | |
| 4,492,231 A | 1/1985 | Auth | |
| 4,492,832 A | 1/1985 | Taylor | |
| 4,545,375 A | 10/1985 | Cline | |
| 4,562,838 A | 1/1986 | Walker | |
| 4,565,200 A | 1/1986 | Cosman | |
| 4,576,177 A | 3/1986 | Webster, Jr. | |
| 4,589,411 A | 5/1986 | Friedman | |
| 4,593,691 A | 6/1986 | Lindstrom et al. | |
| 4,595,809 A | 6/1986 | Pool | |
| 4,606,342 A | 8/1986 | Zamba et al. | |
| 4,608,977 A | 9/1986 | Brown | |
| 4,619,258 A | 10/1986 | Pool | |
| 4,620,548 A | 11/1986 | Hasselbrack | |
| 4,625,723 A | 12/1986 | Altnether et al. | |
| 4,640,279 A | 2/1987 | Beard | |
| 4,642,128 A | 2/1987 | Solorzano | |
| 4,655,215 A | 4/1987 | Pike | |
| 4,657,016 A | 4/1987 | Garito et al. | |
| 4,662,383 A | 5/1987 | Sogawa et al. | |
| 4,683,884 A | 8/1987 | Hatfield et al. | |
| 4,688,569 A | 8/1987 | Rabinowitz | |
| 4,701,193 A | 10/1987 | Robertson et al. | |
| 4,712,544 A | 12/1987 | Ensslin | |
| 4,735,603 A | 4/1988 | Goodson et al. | |
| 4,739,759 A | 4/1988 | Rexworth et al. | |
| 4,741,334 A * | 5/1988 | Irnich | 606/35 |
| 4,754,754 A | 7/1988 | Garito et al. | |
| 4,785,807 A * | 11/1988 | Blanch | 606/45 |
| 4,788,977 A | 12/1988 | Farin et al. | |
| 4,794,215 A | 12/1988 | Sawada et al. | |
| 4,796,623 A | 1/1989 | Krasner et al. | |
| 4,803,323 A | 2/1989 | Bauer et al. | |
| 4,811,733 A | 3/1989 | Borsanyi et al. | |
| 4,827,911 A | 5/1989 | Broadwin et al. | |
| 4,827,927 A | 5/1989 | Newton | |
| 4,832,024 A | 5/1989 | Boussignac et al. | |
| D301,739 S | 6/1989 | Turner et al. | |
| 4,846,790 A | 7/1989 | Hornlein et al. | |
| 4,850,353 A | 7/1989 | Stasz et al. | |
| 4,860,745 A | 8/1989 | Farin et al. | |
| 4,862,889 A | 9/1989 | Feucht | |
| 4,862,890 A | 9/1989 | Stasz et al. | |
| 4,869,715 A | 9/1989 | Sherburne | |
| 4,872,454 A | 10/1989 | DeOliveira et al. | |
| 4,876,110 A | 10/1989 | Blanch | |
| 4,880,719 A | 11/1989 | Murofushi et al. | |
| 4,886,060 A | 12/1989 | Wiksell | |
| 4,901,719 A | 2/1990 | Trenconsky et al. | |
| 4,903,696 A | 2/1990 | Stasz et al. | |
| 4,909,249 A | 3/1990 | Akkas et al. | |
| 4,911,159 A | 3/1990 | Johnson et al. | |
| 4,916,275 A | 4/1990 | Almond | |
| 4,919,129 A | 4/1990 | Weber, Jr. et al. | |
| 4,921,476 A | 5/1990 | Wuchinich | |
| 4,922,903 A | 5/1990 | Welch et al. | |
| 4,931,047 A | 6/1990 | Broadwin et al. | |
| 4,949,734 A | 8/1990 | Bernstein | |
| 4,961,435 A | 10/1990 | Kitagawa et al. | |
| 4,966,597 A | 10/1990 | Cosman | |
| 4,969,885 A | 11/1990 | Farin | |
| 4,986,839 A | 1/1991 | Wertz et al. | |
| 4,988,334 A | 1/1991 | Hornlein et al. | |
| 4,993,430 A | 2/1991 | Shimoyama et al. | |
| 5,000,754 A | 3/1991 | DeOliveira et al. | |
| 5,011,483 A | 4/1991 | Sleister | |
| 5,013,312 A | 5/1991 | Parins et al. | |
| 5,015,227 A | 5/1991 | Broadwin et al. | |
| 5,026,368 A | 6/1991 | Adair | |
| 5,029,588 A | 7/1991 | Yock et al. | |
| 5,035,695 A | 7/1991 | Weber, Jr. et al. | |
| 5,035,696 A | 7/1991 | Rydell | |
| 5,046,506 A | 9/1991 | Singer | |
| 5,055,100 A | 10/1991 | Olsen | |
| 5,071,418 A | 12/1991 | Rosenbaum | |
| 5,074,863 A | 12/1991 | Dines | |
| 5,076,276 A | 12/1991 | Sakurai et al. | |
| 5,088,997 A | 2/1992 | Delahuerga et al. | |
| 5,098,430 A | 3/1992 | Fleenor | |
| 5,100,402 A | 3/1992 | Fan | |
| 5,103,804 A | 4/1992 | Abele et al. | |
| 5,108,391 A | 4/1992 | Flachenecker et al. | |
| 5,133,714 A | 7/1992 | Beane | |
| 5,147,292 A | 9/1992 | Kullas et al. | |
| D330,253 S | 10/1992 | Burek | |
| 5,154,709 A | 10/1992 | Johnson | |
| 5,160,334 A | 11/1992 | Billings et al. | |
| 5,162,044 A | 11/1992 | Gahn et al. | |
| 5,167,659 A | 12/1992 | Ohtomo et al. | |
| 5,178,012 A | 1/1993 | Culp | |
| 5,178,605 A | 1/1993 | Imonti | |
| 5,190,517 A | 3/1993 | Zieve et al. | |
| 5,190,541 A | 3/1993 | Abele et al. | |
| 5,192,267 A | 3/1993 | Shapira et al. | |
| 5,195,959 A | 3/1993 | Smith | |
| 5,196,007 A | 3/1993 | Ellman et al. | |
| 5,197,962 A | 3/1993 | Sansom et al. | |
| 5,199,944 A | 4/1993 | Cosmescu | |
| 5,217,457 A | 6/1993 | Delahuerga et al. | |
| 5,224,944 A | 7/1993 | Elliott | |
| 5,225,741 A | 7/1993 | Auld et al. | |
| 5,226,904 A | 7/1993 | Gentelia et al. | |
| 5,230,623 A | 7/1993 | Guthrie et al. | |
| 5,233,515 A | 8/1993 | Cosman | |
| 5,234,428 A | 8/1993 | Kaufman | |
| 5,234,429 A | 8/1993 | Goldhaber | |
| 5,242,442 A | 9/1993 | Hirschfeld | |
| 5,244,462 A | 9/1993 | Delahuerga et al. | |
| 5,246,438 A | 9/1993 | Langberg | |
| 5,246,440 A | 9/1993 | Van Noord | |
| 5,254,082 A | 10/1993 | Takase | |
| 5,254,117 A | 10/1993 | Rigby et al. | |
| 5,256,138 A | 10/1993 | Burek et al. | |
| 5,261,906 A | 11/1993 | Pennino et al. | |
| 5,267,994 A | 12/1993 | Gentelia et al. | |
| 5,269,781 A | 12/1993 | Hewell, III | |
| 5,281,213 A | 1/1994 | Milder et al. | |
| 5,300,087 A | 4/1994 | Knoepfler | |
| 5,304,763 A | 4/1994 | Ellman et al. | |
| 5,306,238 A | 4/1994 | Fleenor | |
| 5,312,329 A | 5/1994 | Beaty et al. | |
| 5,312,400 A | 5/1994 | Bales et al. | |
| 5,312,401 A | 5/1994 | Newton et al. | |
| 5,318,516 A | 6/1994 | Cosmescu | |
| 5,318,565 A | 6/1994 | Kuriloff et al. | |
| 5,322,503 A | 6/1994 | Desai | |
| 5,323,778 A | 6/1994 | Kandarpa et al. | |
| 5,330,470 A | 7/1994 | Hagen | |
| 5,330,518 A | 7/1994 | Neilson et al. | |
| 5,334,183 A | 8/1994 | Wuchinich | |
| 5,334,193 A | 8/1994 | Nardella | |
| 5,342,356 A | 8/1994 | Ellman et al. | |
| 5,342,357 A | 8/1994 | Nardella | |
| 5,348,554 A | 9/1994 | Imran et al. | |

(56) References Cited

U.S. PATENT DOCUMENTS

| | | |
|---|---|---|
| 5,348,555 A | 9/1994 | Zinnanti |
| 5,366,464 A | 11/1994 | Belknap |
| 5,370,675 A | 12/1994 | Edwards et al. |
| 5,376,089 A | 12/1994 | Smith |
| 5,380,320 A | 1/1995 | Morris |
| 5,382,247 A | 1/1995 | Cimino et al. |
| 5,383,876 A | 1/1995 | Nardella |
| 5,383,917 A | 1/1995 | Desai et al. |
| 5,385,148 A | 1/1995 | Lesh et al. |
| 5,395,363 A | 3/1995 | Billings et al. |
| 5,399,823 A | 3/1995 | McCusker |
| 5,401,273 A | 3/1995 | Shippert |
| 5,403,311 A | 4/1995 | Abele et al. |
| 5,403,882 A | 4/1995 | Huggins |
| 5,406,945 A | 4/1995 | Riazzi et al. |
| 5,409,000 A | 4/1995 | Imran |
| 5,409,006 A | 4/1995 | Buchholtz et al. |
| 5,409,484 A | 4/1995 | Erlich et al. |
| 5,413,575 A | 5/1995 | Haenggi |
| 5,417,686 A | 5/1995 | Peterson et al. |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,433,739 A | 7/1995 | Sluijter et al. |
| 5,437,662 A | 8/1995 | Nardella |
| 5,451,222 A | 9/1995 | De Maagd et al. |
| 5,458,597 A | 10/1995 | Edwards et al. |
| 5,460,602 A | 10/1995 | Shapira |
| 5,462,521 A | 10/1995 | Brucker et al. |
| 5,462,522 A | 10/1995 | Sakurai et al. |
| 5,468,240 A | 11/1995 | Gentelia et al. |
| 5,472,441 A | 12/1995 | Edwards et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,490,850 A | 2/1996 | Ellman et al. |
| 5,496,314 A | 3/1996 | Eggers |
| 5,498,654 A | 3/1996 | Shimasaki et al. |
| 5,500,012 A | 3/1996 | Brucker et al. |
| 5,520,684 A | 5/1996 | Imran |
| D370,731 S | 6/1996 | Corace et al. |
| 5,531,722 A | 7/1996 | Van Hale |
| 5,536,267 A | 7/1996 | Edwards et al. |
| 5,549,604 A | 8/1996 | Sutcu et al. |
| 5,561,278 A | 10/1996 | Rutten |
| 5,562,503 A | 10/1996 | Ellman et al. |
| 5,571,147 A | 11/1996 | Sluijter et al. |
| 5,588,432 A | 12/1996 | Crowley |
| 5,599,345 A | 2/1997 | Edwards et al. |
| 5,599,346 A | 2/1997 | Edwards et al. |
| 5,601,224 A | 2/1997 | Bishop et al. |
| 5,609,573 A | 3/1997 | Sandock |
| 5,626,575 A | 5/1997 | Crenner |
| 5,630,417 A | 5/1997 | Petersen et al. |
| 5,630,426 A | 5/1997 | Eggers et al. |
| 5,630,812 A | 5/1997 | Ellman et al. |
| 5,633,578 A | 5/1997 | Eggers et al. |
| 5,634,912 A | 6/1997 | Injev |
| 5,634,935 A | 6/1997 | Taheri |
| 5,643,197 A | 7/1997 | Brucker et al. |
| 5,643,256 A | 7/1997 | Urueta |
| 5,647,871 A | 7/1997 | Levine et al. |
| D384,148 S | 9/1997 | Monson |
| 5,662,111 A | 9/1997 | Cosman |
| 5,669,907 A | 9/1997 | Platt, Jr. et al. |
| 5,674,219 A | 10/1997 | Monson et al. |
| 5,688,267 A | 11/1997 | Panescu et al. |
| 5,693,044 A | 12/1997 | Cosmescu |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,712,543 A | 1/1998 | Sjostrom |
| 5,713,895 A | 2/1998 | Lontine et al. |
| 5,720,745 A | 2/1998 | Farin et al. |
| D393,067 S | 3/1998 | Geary et al. |
| 5,735,847 A | 4/1998 | Gough et al. |
| 5,749,869 A | 5/1998 | Lindenmeier et al. |
| 5,765,418 A | 6/1998 | Rosenberg |
| 5,775,338 A | 7/1998 | Hastings |
| 5,776,092 A | 7/1998 | Farin et al. |
| 5,788,688 A | 8/1998 | Bauer et al. |
| 5,792,146 A | 8/1998 | Cosman |
| 5,797,907 A | 8/1998 | Clement |
| 5,800,431 A | 9/1998 | Brown |
| 5,836,897 A | 11/1998 | Sakurai et al. |
| 5,836,909 A | 11/1998 | Cosmescu |
| 5,836,944 A | 11/1998 | Cosmescu |
| D402,030 S | 12/1998 | Roberts et al. |
| D402,031 S | 12/1998 | Roberts et al. |
| 5,843,109 A | 12/1998 | Mehta et al. |
| 5,846,236 A | 12/1998 | Lindenmeier et al. |
| 5,848,967 A | 12/1998 | Cosman |
| 5,849,011 A | 12/1998 | Jones et al. |
| 5,859,527 A | 1/1999 | Cook |
| 5,868,740 A | 2/1999 | LeVeen et al. |
| 5,868,768 A | 2/1999 | Wicherski et al. |
| 5,876,400 A | 3/1999 | Songer |
| 5,879,347 A | 3/1999 | Saadat |
| 5,888,200 A | 3/1999 | Walen |
| 5,893,848 A | 4/1999 | Negus et al. |
| 5,893,849 A | 4/1999 | Weaver |
| 5,893,862 A | 4/1999 | Pratt et al. |
| 5,913,864 A | 6/1999 | Garito et al. |
| 5,919,219 A | 7/1999 | Knowlton |
| 5,921,982 A | 7/1999 | Lesh et al. |
| 5,928,159 A | 7/1999 | Eggers et al. |
| 5,938,589 A | 8/1999 | Wako et al. |
| 5,941,887 A | 8/1999 | Steen et al. |
| 5,943,719 A | 8/1999 | Feldman et al. |
| 5,944,737 A | 8/1999 | Tsonton et al. |
| 5,951,546 A | 9/1999 | Lorentzen |
| 5,951,548 A | 9/1999 | DeSisto et al. |
| 5,951,581 A | 9/1999 | Saadat et al. |
| 5,954,686 A | 9/1999 | Garito et al. |
| 5,972,007 A | 10/1999 | Sheffield et al. |
| 6,001,093 A | 12/1999 | Swanson et al. |
| 6,004,318 A | 12/1999 | Garito et al. |
| 6,004,333 A | 12/1999 | Sheffield et al. |
| 6,004,335 A | 12/1999 | Vaitekunas et al. |
| 6,006,126 A | 12/1999 | Cosman |
| 6,010,499 A | 1/2000 | Cobb |
| 6,022,347 A | 2/2000 | Lindenmeier et al. |
| 6,045,564 A | 4/2000 | Walen |
| 6,053,912 A | 4/2000 | Panescu et al. |
| 6,059,780 A | 5/2000 | Gough et al. |
| 6,061,551 A | 5/2000 | Sorrells et al. |
| 6,063,050 A | 5/2000 | Manna et al. |
| 6,068,603 A | 5/2000 | Suzuki |
| 6,068,627 A | 5/2000 | Orszulak et al. |
| 6,070,444 A | 6/2000 | Lontine et al. |
| 6,071,281 A | 6/2000 | Burnside et al. |
| 6,074,386 A | 6/2000 | Goble et al. |
| 6,074,387 A | 6/2000 | Heim et al. |
| 6,074,389 A | 6/2000 | Levine et al. |
| 6,080,149 A | 6/2000 | Huang et al. |
| 6,086,544 A | 7/2000 | Hibner et al. |
| 6,090,123 A | 7/2000 | Culp et al. |
| 6,099,525 A | 8/2000 | Cosmescu |
| 6,106,524 A | 8/2000 | Eggers et al. |
| 6,117,134 A | 9/2000 | Cunningham et al. |
| 6,132,426 A | 10/2000 | Kroll |
| 6,139,547 A | 10/2000 | Lontine et al. |
| D433,752 S | 11/2000 | Saravia |
| 6,142,995 A | 11/2000 | Cosmescu |
| 6,146,353 A | 11/2000 | Platt, Jr. |
| 6,146,380 A | 11/2000 | Racz et al. |
| 6,149,648 A | 11/2000 | Cosmescu |
| 6,156,035 A | 12/2000 | Songer |
| 6,162,216 A | 12/2000 | Guziak et al. |

(56) References Cited

U.S. PATENT DOCUMENTS

| | | | |
|---|---|---|---|
| 6,197,024 B1 | 3/2001 | Sullivan |
| 6,200,311 B1 | 3/2001 | Danek et al. |
| 6,203,541 B1 | 3/2001 | Keppel |
| D441,077 S | 4/2001 | Garito et al. |
| 6,213,999 B1 | 4/2001 | Platt, Jr. et al. |
| 6,214,003 B1 | 4/2001 | Morgan et al. |
| 6,238,388 B1 | 5/2001 | Ellman et al. |
| 6,241,723 B1 | 6/2001 | Heim et al. |
| 6,241,725 B1 | 6/2001 | Cosman |
| 6,241,753 B1 | 6/2001 | Knowlton |
| 6,246,912 B1 | 6/2001 | Sluijter et al. |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,273,862 B1 | 8/2001 | Privitera et al. |
| 6,277,083 B1 | 8/2001 | Eggers et al. |
| 6,286,512 B1 | 9/2001 | Loeb et al. |
| 6,287,305 B1 | 9/2001 | Heim et al. |
| 6,287,344 B1 | 9/2001 | Wampler et al. |
| 6,306,132 B1 | 10/2001 | Moorman et al. |
| 6,312,441 B1 | 11/2001 | Deng |
| 6,325,799 B1 | 12/2001 | Goble |
| D453,222 S | 1/2002 | Garito et al. |
| 6,337,998 B1 | 1/2002 | Behl et al. |
| D453,833 S | 2/2002 | Hess |
| 6,350,276 B1 | 2/2002 | Knowlton |
| 6,352,544 B1 | 3/2002 | Spitz |
| 6,355,034 B2 | 3/2002 | Cosmescu |
| 6,358,281 B1 | 3/2002 | Berrang et al. |
| 6,361,532 B1 | 3/2002 | Burek |
| D457,955 S | 5/2002 | Bilitz |
| 6,386,032 B1 | 5/2002 | Lemkin et al. |
| 6,395,001 B1 | 5/2002 | Ellman et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,725 B1 | 6/2002 | Khandkar et al. |
| 6,413,255 B1 | 7/2002 | Stern |
| 6,416,491 B1 | 7/2002 | Edwards et al. |
| 6,416,509 B1 | 7/2002 | Goble et al. |
| 6,425,912 B1 | 7/2002 | Knowlton |
| 6,432,070 B1 | 8/2002 | Talish et al. |
| 6,458,122 B1 | 10/2002 | Pozzato |
| 6,458,125 B1 | 10/2002 | Cosmescu |
| 6,461,352 B2 | 10/2002 | Morgan et al. |
| 6,464,702 B2 | 10/2002 | Schulze et al. |
| 6,471,659 B2 | 10/2002 | Eggers et al. |
| 6,478,793 B1 | 11/2002 | Cosman et al. |
| 6,494,882 B1 | 12/2002 | Lebouitz et al. |
| 6,500,169 B1 | 12/2002 | Deng |
| 6,500,172 B1 | 12/2002 | Panescu et al. |
| 6,506,189 B1 | 1/2003 | Rittman, III et al. |
| 6,511,479 B2 | 1/2003 | Gentelia et al. |
| 6,526,320 B2 | 2/2003 | Mitchell |
| 6,530,922 B2 | 3/2003 | Cosman et al. |
| 6,551,313 B1 | 4/2003 | Levin |
| 6,558,383 B2 | 5/2003 | Cunningham et al. |
| 6,575,969 B1 | 6/2003 | Rittman, III et al. |
| 6,585,664 B2 | 7/2003 | Burdorff et al. |
| 6,589,239 B2 | 7/2003 | Khandkar et al. |
| 6,605,085 B1 | 8/2003 | Edwards |
| 6,610,054 B1 | 8/2003 | Edwards et al. |
| 6,610,057 B1 | 8/2003 | Ellman et al. |
| 6,613,047 B2 | 9/2003 | Edwards |
| 6,616,658 B2 | 9/2003 | Ineson |
| 6,618,626 B2 | 9/2003 | West, Jr. et al. |
| 6,620,161 B2 | 9/2003 | Schulze et al. |
| 6,632,193 B1 | 10/2003 | Davison et al. |
| 6,652,514 B2 | 11/2003 | Ellman et al. |
| 6,662,053 B2 | 12/2003 | Borkan |
| 6,669,691 B1 | 12/2003 | Taimisto |
| 6,679,881 B1 | 1/2004 | Bybee |
| 6,685,701 B2 | 2/2004 | Orszulak et al. |
| 6,685,704 B2 | 2/2004 | Greep |
| 6,685,729 B2 | 2/2004 | Gonzalez |
| 6,702,812 B2 | 3/2004 | Cosmescu |
| 6,710,546 B2 | 3/2004 | Crenshaw |
| 6,712,813 B2 | 3/2004 | Ellman et al. |
| 6,719,746 B2 | 4/2004 | Blanco |
| 6,740,079 B1 | 5/2004 | Eggers et al. |
| 6,747,218 B2 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,770,070 B1* | 8/2004 | Balbierz .................... 606/41 |
| 6,794,929 B2 | 9/2004 | Pelly |
| 6,830,569 B2 | 12/2004 | Thompson et al. |
| 6,840,948 B2 | 1/2005 | Albrecht et al. |
| 6,855,140 B2 | 2/2005 | Albrecht et al. |
| 6,902,536 B2 | 6/2005 | Manna et al. |
| 6,905,496 B1 | 6/2005 | Ellman et al. |
| 6,923,804 B2 | 8/2005 | Eggers et al. |
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| 7,033,353 B2 | 4/2006 | Stoddard et al. |
| D521,641 S | 5/2006 | Reschke et al. |
| 7,137,980 B2 | 11/2006 | Buysse et al. |
| D535,396 S | 1/2007 | Reschke et al. |
| 7,156,842 B2 | 1/2007 | Sartor et al. |
| 7,179,255 B2 | 2/2007 | Lettice et al. |
| 7,186,222 B1 | 3/2007 | Callister et al. |
| 7,207,989 B2 | 4/2007 | Pike, Jr. et al. |
| 7,217,269 B2 | 5/2007 | El-Galley et al. |
| 7,218,958 B2 | 5/2007 | Rashidi |
| 7,235,070 B2 | 6/2007 | Vanney |
| 7,235,073 B2 | 6/2007 | Levine et al. |
| 7,238,184 B2 | 7/2007 | Megerman et al. |
| 7,264,619 B2 | 9/2007 | Venturelli |
| 7,278,991 B2 | 10/2007 | Morris et al. |
| 7,294,127 B2 | 11/2007 | Leung et al. |
| 7,294,143 B2 | 11/2007 | Francischelli |
| 7,302,285 B2 | 11/2007 | Fuimaono et al. |
| 7,303,558 B2 | 12/2007 | Swanson |
| 7,331,947 B2 | 2/2008 | McGuckin, Jr. et al. |
| RE40,156 E | 3/2008 | Sharps et al. |
| 7,341,586 B2 | 3/2008 | Daniel et al. |
| 7,344,533 B2 | 3/2008 | Pearson et al. |
| 7,364,578 B2 | 4/2008 | Francischelli et al. |
| 7,364,579 B2 | 4/2008 | Mulier et al. |
| 7,367,974 B2 | 5/2008 | Haemmerich et al. |
| 7,367,975 B2 | 5/2008 | Malecki et al. |
| 7,387,625 B2 | 6/2008 | Hovda et al. |
| 7,419,486 B2 | 9/2008 | Kampa |
| 7,419,487 B2 | 9/2008 | Johnson et al. |
| 7,419,488 B2 | 9/2008 | Ciarrocca et al. |
| 7,419,489 B2 | 9/2008 | Vanney et al. |
| 7,422,587 B2 | 9/2008 | Bek et al. |
| 2001/0034518 A1 | 10/2001 | Edwards et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058933 A1 | 5/2002 | Christopherson et al. |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0111615 A1 | 8/2002 | Cosman et al. |
| 2002/0111622 A1 | 8/2002 | Khandkar et al. |
| 2002/0120261 A1 | 8/2002 | Morris et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |

(56) References Cited

U.S. PATENT DOCUMENTS

| | | | |
|---|---|---|---|
| 2002/0156472 A1 | 10/2002 | Lee et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0018247 A1 | 1/2003 | Gonzalez |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0114850 A1* | 6/2003 | McClurken et al. ............ 606/50 |
| 2003/0114851 A1* | 6/2003 | Truckai et al. .................. 606/51 |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0002745 A1 | 1/2004 | Fleming et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki |
| 2004/0034346 A1 | 2/2004 | Stern et al. |
| 2004/0039429 A1 | 2/2004 | Daniel et al. |
| 2004/0054370 A1 | 3/2004 | Given |
| 2004/0092927 A1 | 5/2004 | Podhajsky et al. |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0181216 A1 | 9/2004 | Kelly et al. |
| 2004/0199161 A1 | 10/2004 | Truckai et al. |
| 2004/0230262 A1 | 11/2004 | Sartor et al. |
| 2004/0236323 A1 | 11/2004 | Schoenman et al. |
| 2004/0243120 A1 | 12/2004 | Orszulak et al. |
| 2004/0254573 A1 | 12/2004 | Dycus |
| 2004/0267252 A1 | 12/2004 | Washington et al. |
| 2004/0267254 A1 | 12/2004 | Manzo et al. |
| 2004/0267256 A1 | 12/2004 | Garabedian et al. |
| 2004/0267297 A1 | 12/2004 | Malackowski |
| 2005/0010209 A1 | 1/2005 | Lee et al. |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096651 A1* | 5/2005 | Truckai et al. .................. 606/51 |
| 2005/0096681 A1 | 5/2005 | Desinger et al. |
| 2005/0107782 A1 | 5/2005 | Reschke |
| 2005/0107784 A1 | 5/2005 | Moses |
| 2005/0107785 A1 | 5/2005 | Dycus |
| 2005/0113817 A1 | 5/2005 | Isaacson et al. |
| 2005/0113818 A1 | 5/2005 | Sartor et al. |
| 2005/0113823 A1 | 5/2005 | Reschke et al. |
| 2005/0113824 A1 | 5/2005 | Sartor et al. |
| 2005/0113825 A1 | 5/2005 | Cosmescu |
| 2005/0113826 A1* | 5/2005 | Johnson et al. .................. 606/45 |
| 2005/0119655 A1 | 6/2005 | Moses |
| 2005/0149001 A1 | 7/2005 | Uchikubo et al. |
| 2005/0154385 A1 | 7/2005 | Heim et al. |
| 2005/0154387 A1 | 7/2005 | Moses |
| 2005/0155743 A1 | 7/2005 | Getz, Jr. et al. |
| 2005/0192564 A1 | 9/2005 | Cosman et al. |
| 2006/0041257 A1 | 2/2006 | Sartor et al. |
| 2006/0058783 A1 | 3/2006 | Buchman |
| 2006/0064084 A1* | 3/2006 | Haemmerich et al. .......... 606/41 |
| 2006/0079885 A1 | 4/2006 | Rick et al. |
| 2006/0079886 A1* | 4/2006 | Orszulak et al. ................. 606/41 |
| 2006/0079887 A1 | 4/2006 | Buysse |
| 2006/0178667 A1 | 8/2006 | Sartor et al. |
| 2007/0049926 A1 | 3/2007 | Sartor |
| 2007/0093810 A1 | 4/2007 | Sartor |
| 2007/0260240 A1 | 11/2007 | Rusin |
| 2008/0021448 A1 | 1/2008 | Orszulak |
| 2008/0027424 A1 | 1/2008 | DeCarlo et al. |
| 2008/0183165 A1 | 7/2008 | Buysse et al. |

FOREIGN PATENT DOCUMENTS

| | | |
|---|---|---|
| DE | 24 60 481 A1 | 6/1976 |
| DE | 30 45 996 | 7/1982 |
| DE | 10224154 | 12/2003 |
| EP | 0171967 A | 2/1986 |
| EP | 0186369 A | 7/1986 |
| EP | 0246350 | 11/1987 |
| EP | 0310431 | 4/1989 |
| EP | 0608609 | 8/1994 |
| EP | 1050277 | 11/2000 |
| EP | 1050279 | 11/2000 |
| EP | 1 070 518 A2 | 1/2001 |
| EP | 1082945 | 3/2001 |
| EP | 1293171 | 3/2003 |
| EP | 1465037 A | 10/2004 |
| EP | 1 645 233 | 4/2006 |
| EP | 1645234 | 4/2006 |
| EP | 1656900 | 5/2006 |
| EP | 1852078 | 11/2007 |
| FR | 2235669 | 1/1975 |
| FR | 2798579 | 3/2001 |
| FR | 2864439 | 7/2005 |
| WO | WO 93/24066 | 12/1993 |
| WO | WO94/20032 | 9/1994 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |
| WO | WO 96/39086 | 12/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 98/43264 | 10/1998 |
| WO | WO 99/01074 | 1/1999 |
| WO | WO 99/04710 | 2/1999 |
| WO | WO 99/22657 | 5/1999 |
| WO | WO 00/67846 | 11/2000 |
| WO | WO 01/00114 A1 | 1/2001 |

(56) References Cited

FOREIGN PATENT DOCUMENTS

| WO | WO01/64122 | 9/2001 |
|---|---|---|
| WO | WO 02/47568 A1 | 6/2002 |
| WO | WO 2004/010883 A1 | 2/2004 |
| WO | WO 2004/045436 | 6/2004 |
| WO | WO 2004/073753 A2 | 9/2004 |
| WO | WO 2005/009528 | 2/2005 |
| WO | WO 2005/060849 A1 | 7/2005 |

OTHER PUBLICATIONS

International Search Report from Application No. EP 08 02 1070 dated Apr. 1, 2009.
Zucker, Karl, Surgical Laparoscopy, Lippincott Williams & Wilkins, Ed. 2, 2001 (2 pages).
International Search Report from European Application No. EP 08 00 2357 dated Jun. 30, 2008.
McRury, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.
International Search Report EP 06 005 540.7 dated Sep. 24, 2007.
European Search Report from Application EP 07009028 dated Jul. 16, 2007.
Bulletin of the American Physical Society, vol. 47, No. 5, Aug. 2002.
European Search Report from Application EP 06019768 dated Jan. 8, 2007.
European Search Report from Application EP 05025424 dated Jan. 23, 2007.
European Search Report from Application EP 05025423.4 dated Jan. 12, 2007.
International Search Report from EP 06 01 4461 dated Oct. 31, 2006.
Cosman ER, Cosman BJ: "Methods of Making Nervous System Lesions", in William RH, Rengachary SS (eds): Neurosurgery. New York: McGraw-Hill, vol. 111, pp. 2490-2498, 1984.
Anderson, Gary et al., "A numerical study of rapid heating for high temperature radio frequency hyperthermia", International Journal of Bio-Medical Computing, 35 (1994) 297-307.
Goldberg, et al., "Tissue Ablation with Radiofrequency: Effective Probe Size, Gauge, Duration and Temperature and Lesion Volume", Acad Radio, 1995, vol. 2, No. 5, pp. 399-404.
Melvin A. Astrahan, "A Localized Current Field Hyperthermia System for Use with 192-Iridium Interstitial Implants", Medical Physics, 9(3), May/Jun. 1982.
Cosman et al. "Theoretical Aspects of Radiofrequency Lesions in the Dorsal Root Entry Zone". Neurosurgery 15:945.950, 1984.
Stuart W. Young, Nuclear Magnetic Resonance Imaging—Basic Principles, Raven Press, New York, 1984.
E.R. Cosman, et al., "Radiofrequency Lesion Generation and its Effect on Tissue Impedence", Applied Neurophysiology, 51:230-242, 1988.
K. Ogata, Modern Control Engineering, Prentice-Hall, Englewood Cliffs, N.J., 1970.
E. Alexander et al., "Magnetic resonance image-directed stereotactic neurosurgery: use of image fusion with computerized tomography to enhance spatial accuracy", J. Neurosurg., 83:271, 276, 1995.
Reidenbach (1995) "First Experimental Results with Special Applicators for High-Frequency Interstitial Thermotherapy", Society Minimally Ivasive Therapy, 4(Suppl 1) :40 (Abstr).
Organ LW. (1976) "Electrophysiologic Principles of Radiofrequency Lesion Making" Appl. Neumphysiol, vol. 39: pp. 69-76.
Livraghi et al. (1995) "Saline-enhanced RF Tissue Ablation in the Treatment of Liver Metastases", Radiology, 205-210.
Solbiati et al. (1995) "Percutaneous US-guided RF Tissue Ablation of Liver Metastases: Long-term Follow-up", Radiology, 197(P): 199.
Solbiati, et al. (2001) "Percutaneous Radio-frequency Ablation of Hepatic Metastases from Colorectal Cancer: Long-term Results in 117 Patients", *Radiology*, vol. 221, pp. 159-166.
Goldberg, et al., "Image-guided Radiofrequency Tumor Ablation: Challenges and Opportunities—Part I", (2001) *J Vasc. Interv. Radiol*, vol. 12, pp. 1021-1032.
McGahan et al. (1995) "Percutaneous Ultrasound-guided Radiofrequency Electrocautery Ablation of Prostate Tissue in Dogs", Acad Radiol, vol. 2, No. 1:pp. 61-65.
Goldberg et al. (1995) "Tissue Ablation with Radiofrequency Using Multiprobe Arrays", Acad Radiol, vol. 2: pp. 399-404.
Goldberg et al. (1995) "Saline-enhanced RF Ablation: Demonstration of Efficacy and Optimization of Parameter", Radiology, 197(P): 140 (Abstr).
European Search Report from Application EP 05021935 dated Jan. 27, 2006.
European Search Report from Application EP 05021939 dated Jan. 27, 2006.
European Search Report from Application EP 05021025 dated Mar. 13, 2006.
European Search Report from Application EP 05021936.9 dated Feb. 6, 2006.
International Search Report from PCT/US03/37111; Jul. 21, 2004.
International Search Report from PCT/US04/04685; Aug. 6, 2004.
International Search Report from EP/0401/5980; Sep. 30, 2004.
International Search Report from PCT/US03/22900; Nov. 20, 2003.
International Search Report from EP 05019882.9 dated Feb. 16, 2006.
International Search Resort from EP 05021777.7 dated Feb. 23, 2006.

\* cited by examiner

SOFT TISSUE RF TRANSECTION AND RESECTION DEVICE

CROSS REFERENCE TO RELATED APPLICATIONS

The present application is a continuation of U.S. application Ser. No. 11/418,879, filed on May 5, 2006, now abandoned the disclosure of which is incorporated herein by reference in its entirety.

BACKGROUND

1. Technical Field

The present disclosure is directed to electrosurgical systems and methods and, more particularly, to soft tissue RF transection and resection devices and methods of using the same.

2. Background

Electrosurgical methods are widely used in the operative field since they generally reduce patient bleeding associated with tissue cutting, transecting and/or resecting procedures and improve the surgeons' ability to view the surgical site. Two widely accepted methods of electrosurgery are performed, namely, monopolar electrosurgery and bipolar electrosurgery.

Monopolar electrosurgery methods generally direct electric current along a defined path from an exposed or active electrode through the patient's body to a return pad or electrode, which is externally attached to a suitable location on the patient's skin.

Alternatively, bipolar electrosurgery methods generally direct electric current along a defined path from a first exposed or active electrode through the patient's body to a second exposed or return electrode. Both the first and the second electrodes are typically disposed within the body of the patient.

Transection and/or resection of soft tissues, such as the liver or spleen, pose particular difficulties during electrosurgical operation as compared to electrosurgical operation of other tissues and thus require unique electrosurgical instruments, systems, techniques and the like for operating thereon.

SUMMARY

The present disclosure is directed to electrosurgical systems and methods and, more particularly, to soft tissue RF transection and resection devices and methods of using the same.

According to an aspect of the present disclosure, an electrosurgical system for transecting or resecting a target tissue is provided. The electrosurgical system includes an electrosurgical generator including an active terminal and a return terminal; a first electrically conductive element electrically connectable to the active terminal of the electrosurgical generator, the first electrically conductive element being selectively movable between a first location of a target tissue and a second location of the target tissue; a second electrically conductive element electrically connectable to the active terminal of the electrosurgical generator, the second electrically conductive element configured to couple to the first location of the target tissue; and a third electrically conductive element electrically connectable to the return terminal of the electrosurgical generator, the third electrically conductive element configured to couple to the second location of the target tissue.

According to a further aspect of the present disclosure, a method of performing an electrosurgical procedure on a target tissue is provided. The method includes the steps of providing an electrosurgical system having an electrosurgical generator having an active and a return terminal; a first electrosurgical device electrically connectable to the active terminal of the electro surgical generator, the first electrosurgical device being selectively movable along target tissue; a second electrosurgical device electrically connectable to the active terminal of the electrosurgical generator, the second electrosurgical device being selectively connectable to a first location of the target tissue; and a third electrosurgical device electrically connectable to the return terminal of the electrosurgical generator, the third electrosurgical device being selectively connectable to a second location of the target tissue.

The method further includes the steps of coupling the second electrosurgical device to the first location of the target tissue; coupling the third electrosurgical device to the second location of the target tissue, wherein a resection line is defined between the first location and the second location; and moving the first electrosurgical device substantially along the resection line to desiccate or divide the target tissue.

According to yet another aspect of the present disclosure, a further method of performing an electrosurgical procedure on a target tissue is provided. The present method includes the steps of coupling a second electrosurgical device to a first location of a target tissue; coupling a third electrosurgical device to a second location of the target tissue; causing RF energy to flow between the first location and the second location; coupling a first electrosurgical device at or substantially near the first location; and moving the first electrosurgical device from the first location to the second location.

It is an advantage of the present disclosure to provide a system and method for performing a bipolar tissue transection and/or resection.

It is a further advantage of the present disclosure to provide a system and method to more efficiently desiccate and/or divide tissue using bipolar electrosurgical concepts.

For a better understanding of the present invention and to show how it may be carried into effect, reference will be made by way of example to the accompanying drawings.

BRIEF DESCRIPTION OF THE DRAWINGS

In the drawings, which constitute a part of the specification, exemplary embodiments exhibiting various objectives and features hereof are set forth, specifically.

DETAILED DESCRIPTION OF EMBODIMENTS

Figure 1:
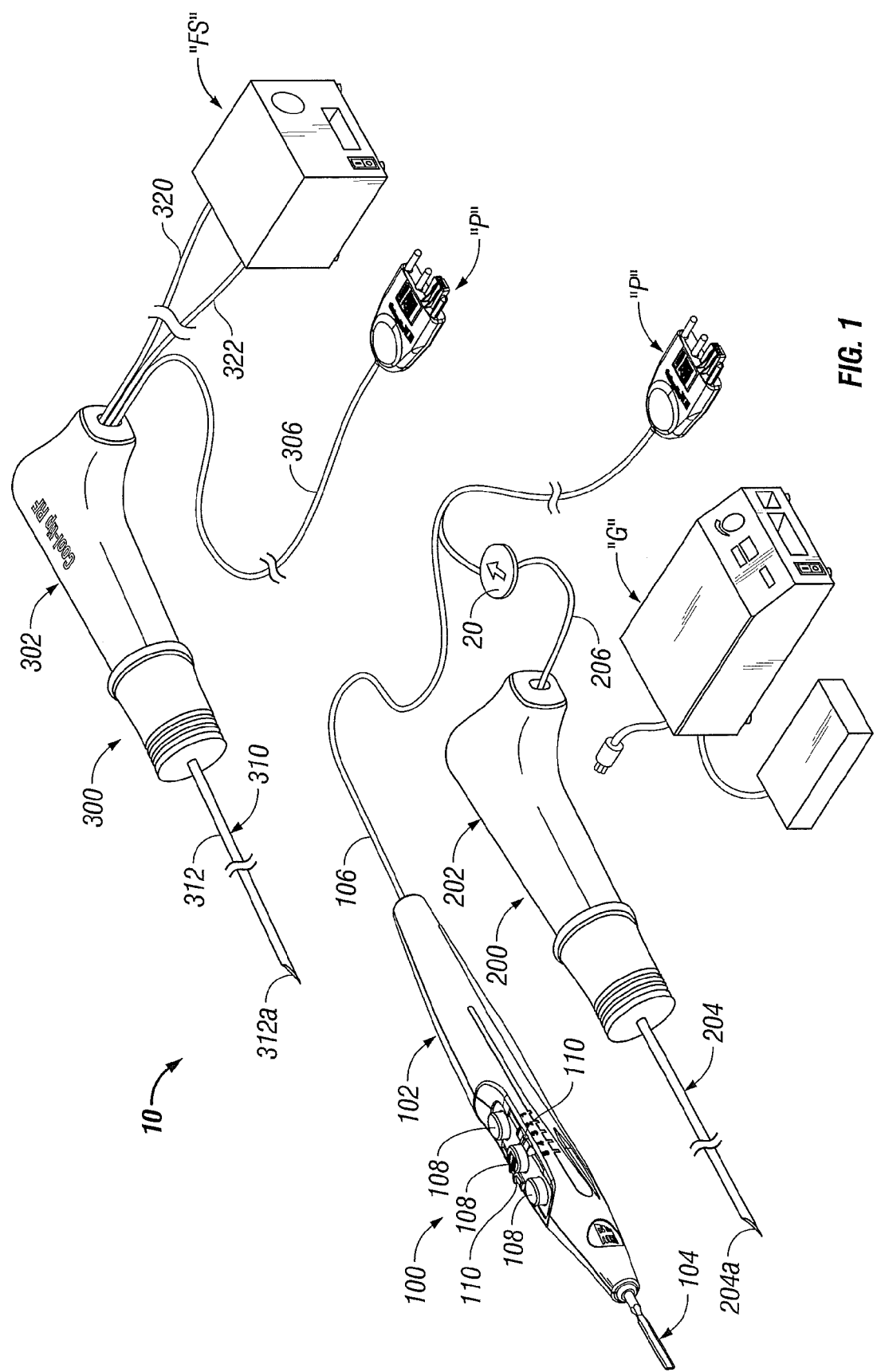
FIG. 1 is a perspective view of an electrosurgical system in accordance with one embodiment of the present disclosure.

Embodiments of electrosurgical systems, in accordance with the present disclosure, are described in detail with reference to the drawings figures wherein like reference numerals identify similar or identical structural elements. As shown in the drawings and described throughout the following description, as is traditional when referring to relative positioning on a surgical instrument, device or apparatus, the term "proximal" refers to the end of the instrument, apparatus or device that is closer to the user and the term "distal" refers to the end of the apparatus that is further away from the user.

FIG. 1 sets forth a perspective view of an electrosurgical system 10 in accordance with an embodiment of the present disclosure. As seen in FIG. 1, electrosurgical system 10 includes a first electrosurgical device 100 and a second electrosurgical device 200 electrically connected in parallel to first electrosurgical device 100. The first electrosurgical device 100 and second electrosurgical device 200 may be connected to or connectable to an electrosurgical generator "G", via a common plug or connector "P" or two individual plugs (not shown) connected in a parallel circuit. While a single common plug "P" is shown for first and second electrosurgical devices 100, 200, it is within the scope of the present disclosure for each of the first and second electrosurgical devices 100, 200 to have a respective plug or the like for electrical connection to the electrosurgical generator "G".

In the illustrated embodiment, the first electrosurgical device 100 includes a housing or handle assembly 102, an electrode blade 104 supported within and extending from a distal end of housing 102, a cable 106 extending from a proximal end of housing 102, and optionally at least one activation switch 108 supported on housing 102. Blade 104 is electrically connected to cable 106. Blade 104 may be fabricated from a suitable electrically conductive material. Each activation switch 108 may function to control the transmission of RF electrical energy supplied from generator "G" to electrosurgical blade 104. While electrode blade 104 is shown and described as a blade, it is within the scope of the present disclosure for electrode blade 104 to be any suitable electrode having any suitable geometry or configuration, such as, for example, a loop, a ball, etc.

Reference may be made to U.S. application Ser. No. 11/337,990, filed on Jan. 24, 2006, the entire contents of which are incorporated herein by reference, for a more detailed discussion of the first electrosurgical device 100. Other suitable electrosurgical devices are contemplated by the present disclosure.

In the illustrated embodiment, the second electrosurgical device 200 includes a housing or handle assembly 202, a needle electrode 204 supported within and extending from a distal end of housing 202, and a cable 206 extending from a proximal end or side of housing 202. Electrode 204 is electrically connected to cable 206. Electrode 204 may terminate in a sharpened distal tip 204a, which is constructed so as to penetrate tissue with a minimum risk of hemorrhage from the puncture tract. Needle electrode 204 may be fabricated from a suitable electrically conductive material and may include an insulative layer covering at least a portion of the length thereof. In an embodiment, a distal end portion of needle electrode 204 may be exposed. Accordingly, since the distal end portion of needle electrode 204 is exposed or non-insulated, the distal end portion is capable of DC or AC delivery, preferably RF delivery.

While the second electrosurgical device 200 is shown as including a needle electrode 204, it is within the scope of the present disclosure for the second electrosurgical device 200 to include any suitable electrically conductive element that is configured to couple to a target tissue. For example, the second electrosurgical device 200 may include a contact pad, an array of needle electrodes, a clamp or clip, or any other electrically conductive element that may contact, be inserted into, may grab onto, the target tissue.

As described above, cable 106 and cable 206 may join together and/or combine into a single cable that is connected to plug "P". Accordingly, the first electrosurgical device 100 and the second electrosurgical device 200 are electrically joined in parallel to one another when connected to generator "G" and when in operative engagement with target tissue.

It one embodiment, a potentiometer 20 may be placed along a cable of any of or each electrosurgical device. Potentiometer 20 may be configured to vary the current and/or voltage being transmitted to needle electrode of the electrosurgical device or devices.

With continued reference to FIG. 1, electrosurgical system 10 further includes a third electrosurgical device 300. In the illustrated embodiment, the third electrosurgical device 300 includes a housing or handle assembly 302, at least one needle electrode assembly 310 supported within and extending from a distal end of handle 302, and a cable 306 extending from a proximal end or a side of housing 302. A plug "P" is provided at the end of cable 306 and functions to electrically connect the third electrosurgical device 300 to electrosurgical generator "G".

Needle electrode assembly 310 may be fabricated from a suitable electrically conductive material and may include an insulative layer covering at least a portion of the length thereof.

In the illustrated embodiment, needle electrode assembly 310 includes an outer tube 312 having at least an exposed distal end portion terminating in a sharpened distal tip 312a, which is constructed so as to penetrate tissue with a minimum risk of hemorrhage from the puncture tract. Outer tube 312 includes a proximal end portion supported in housing 302. Outer tube 312 is hollow and defines a cavity therein that is in fluid communication with a distal end of an outflow conduit 320. Since the distal end portion of outer tube 312 is exposed or non-insulated, the distal end portion is capable of DC or AC delivery, preferably RF delivery.

Needle electrode assembly 312 further includes an inner tube (not explicitly shown) disposed substantially co-axially within the cavity of outer tube 312. The inner tube includes a distal end portion located near the distal end portion of outer tube 312 and a proximal end portion that extends from the proximal end portion of outer tube 312 and that is in fluid communication with a distal end of an inflow conduit 322.

As mentioned above, an inflow conduit 322 includes a distal end that is in fluid communication with the inner tube and a proximal end that extends from housing 302 and is fluidly connected to or connectable to a fluid source "FS". An outflow conduit 320 includes a distal end that is in fluid communication with the cavity of outflow conduit 320 and a proximal end that extends from housing 302 and is fluidly connected to or connectable to fluid source "FS".

In use, a cooling fluid is delivered to distal tip 312a of outer tube 312 from the inner tube and inflow conduit 322 and away from distal tip 312a of outer tube 312 through the cavity of outflow conduit 320. Circulation of the cooling fluid may be established with the use of a suitable pump (not explicitly shown).

While the third electrosurgical device 300 is shown as including a needle electrode assembly 312, it is within the scope of the present disclosure for the third electrosurgical device 300 to include any suitable electrically conductive element that is configured to couple to a target tissue. For example, the third electrosurgical device 300 may include a contact pad, an array of needle electrodes, a clamp or clip, or any other electrically conductive element that may contact, be inserted into, may grab onto, the target tissue.

Reference may be made to U.S. application Ser. No. 11/495,033, filed on Jul. 28, 2006, now U.S. Pat. No. 7,763,018, the entire contents of which are incorporated herein by reference, for a more detailed discussion of the third electrosurgical device 300.

In operation, the first and second electrosurgical devices 100 and 200 may be electrically connected to an active terminal of generator "G", while the third electrosurgical device 300 may be electrically connected to the return electrode of generator "G".

Figure 2:
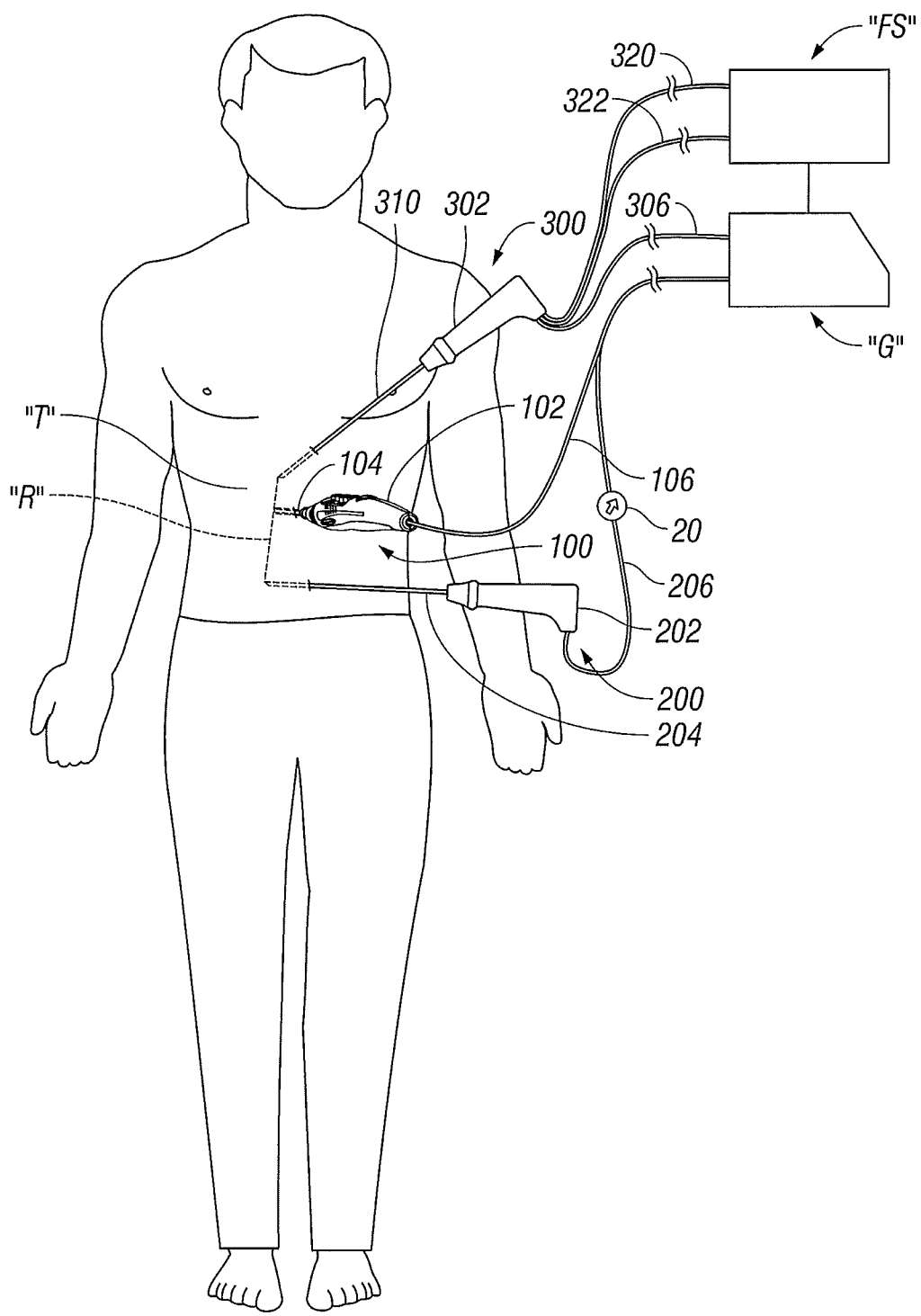
FIG. 2 is a schematic illustration of the electrosurgical system of FIG. 1 being used to perform an electrosurgical procedure on an exemplary body tissue.

Turning now to FIG. 2, a method of using electrosurgical system 10 for transecting and/or resecting tissue is described according to one embodiment of the disclosure. With the patient opened, e.g., the skin of the patient has been cut open to expose the inner tissue "T" of an operating cavity, needle electrode 204 of the second electrosurgical device 200 and needle electrode assembly 310 of the third electrosurgical device 300 are percutaneously inserted into the tissue "T". The line defined between needle electrode 204 of the second electrosurgical device 200 and needle electrode assembly 310 of the third electrosurgical device 300 is denoted as a resection line "R". Accordingly, needle electrode 204 of the second electrosurgical device 200 and needle electrode assembly 310 of the third electrosurgical device 300 may be suitably positioned relative to one another so as to orient and define the direction and length of the resection line "R".

In operation, when generator "G" is activated, RF energy flows between needle electrode 204 of the second electrosurgical device 200 and needle electrode assembly 310 of the third electrosurgical device 300. With needle electrode 204 of the second electrosurgical device 200 and needle electrode assembly 310 of the third electrosurgical device 300 operatively positioned in tissue "T" and activated, blade electrode 104 of the first electrosurgical 100 may be brought into contact with tissue "T" at or substantially near the resection line "R" in order to desiccate and/or divide ablate tissue "T". As described above, the first electrosurgical device 100 and the second electrosurgical device 200 are connected in parallel with one another.

In order to aid the surgeon in making the cut along the resection line "R", a visible line may be drawn or superimposed on a computer screen (not shown) between needle electrode 204 of the second electrosurgical device 200 and needle electrode assembly 310 of the third electrosurgical device 300 in order to approximate the resection line "R".

In operation, contact of blade electrode 104 of first electrosurgical device 100 with tissue "T" creates a short circuit to needle electrode assembly 310 of the third electrosurgical device 300. Accordingly, a majority of the RF energy flows between blade electrode 104 of the first electrosurgical device 100 and needle electrode assembly 310 of the third electrosurgical device 300, which results in relatively faster cutting and/or ablating of tissue "T". According to one method of the present disclosure, blade electrode 104 of first electrosurgical device 100 is initially brought into contact with the resection line "R" in close proximity to needle electrode assembly 310 of the third electrosurgical device 300 and then moved along the resection line "R" toward needle electrode 204 of the second electrosurgical device 200.

As blade electrode 104 of the first electrosurgical device 100 is moved along the resection line "R", toward needle electrode 204 of the second electrosurgical device 200, the RF energy ablates the tissue "T" disposed between the blade electrode 104 of the first electrosurgical device 100 and the needle electrode assembly 310 of the third electrosurgical device 300.

As blade electrode 104 of the first electrosurgical device 100 is progressed or moved through tissue "T", the tissue surrounding blade electrode 104 becomes cooked, thus increasing the impedance of the tissue. As a result, since needle electrode 204 of the second electrosurgical device 200 is connected in parallel with blade electrode 104 of the first electrosurgical device 100, more RF energy is caused to flow between blade electrode 104 of the first electrosurgical device 100 and needle electrode assembly 310 of the third electrosurgical device 300. In this manner, RF energy delivery to the tissue "T" is maximized with lower impedance loads on generator "G" and no relatively high impedance shut-offs are experienced.

When blade electrode 104 is removed or lifted from tissue "T", RF energy once again flows between needle electrode 204 of the second electrosurgical device 200 and needle electrode assembly 310 of the third electrosurgical device 300, thereby preventing impedance cut-out and/or deactivation of generator "G".

It one embodiment, a cooling fluid may be circulated through needle electrode assembly 310 of third electrosurgical device 300, in the manner described above. The cooling fluid prevents charring of tissue "T" around needle electrode assembly 310 and also function to maintain the impedance low.

Any suitable number of needle electrodes connected to the active terminal of electrosurgical generator "G" and inserted in the tissue "T" may be used in the electrosurgical procedure. In addition, any suitable number of needle electrode assemblies connected to the return terminal of electrosurgical generator "G" and inserted in the tissue "T" may be used in the electrosurgical procedure.

The foregoing description is merely a disclosure of particular embodiments and is no way intended to limit the scope of the invention. Other possible modifications are apparent to those skilled in the art and all modifications are to be defined by the following claims.

What is claimed is:

1. A method for performing an electrosurgical procedure on a target tissue, the method comprising:
    providing an electrosurgical system comprising:
        an electrosurgical generator including an active terminal and a return terminal;
        a first electrosurgical device including a first electrically conductive element electrically connectable to the active terminal of the electrosurgical generator;
        a second electrosurgical device including a second electrically conductive element electrically connectable to the active terminal of the electrosurgical generator; and
        a third electrosurgical device including a third electrically conductive element electrically connectable to the return terminal of the electrosurgical generator;
    simultaneously transmitting energy to the first, second, and third electrically conductive elements;
    inserting the second electrically conductive element into a first location of the target tissue;
    inserting the third electrically conductive element into a second location of the target tissue;
    orienting and defining a direction and a length of a single resection line between the second and third electrically conductive elements which are independently positionable with respect to each other on the target tissue, such that axes of the second and third electrically conductive elements are non-parallel with respect to each other; and
    moving the first electrically conductive element along the single resection line to desiccate or divide the target tissue when the second and third electrically conductive elements are inserted into the target tissue, an axis of the first electrically conductive element configured to move in a non-parallel manner with respect to the axes of the second and third electrically conductive elements.

2. The method according to claim 1, wherein moving along the single resection line causes a degree of energy transmission to change.

3. The method according to claim 1, further comprising causing radiofrequency (RF) energy to flow between the second and third electrosurgical devices by removing the first electrosurgical device from the target tissue.

4. The method according to claim 1, further comprising connecting the first and second electrosurgical devices in parallel.

5. The method according to claim 1, further comprising circulating a fluid through the third electrosurgical device.

6. The method according to claim 1, wherein the first electrically conductive element is a blade, the second electrically conductive element includes at least one needle electrode and the third electrically conductive element includes at least one hollow needle electrode assembly.

7. The method according to claim 6, further comprising circulating a fluid through the at least one hollow needle electrode assembly of the third electrosurgical device.

8. The method according to claim 1, wherein the first electrically conductive element is a blade electrode configured to be laterally movable along the single resection line to effect cutting therealong.

9. The method according to claim 8, wherein the first electrically conductive element is associated with an electrosurgical pencil including a handle for supporting the blade electrode.

10. A method for performing an electrosurgical procedure on a target tissue, the method comprising:
   providing an electrosurgical system comprising:
      a generator including an active terminal and a return terminal;
      a first electrosurgical device connected to the active terminal;
      a second electrosurgical device connected to the return terminal; and
      a third electrosurgical device;
   simultaneously transmitting electrical energy to the first, second, and third electrosurgical devices;
   orienting and defining a direction and a length of a single resection line between the second and third electrosurgical devices which are independently positionable with respect to each other on the target tissue, such that axes of the second and third electrically conductive elements are non-parallel with respect to each other; and
   moving the first electrosurgical device along the single resection line to desiccate or divide the target tissue when the second and third electrically conductive elements are inserted into the target tissue, the first electrically conductive element configured to move in a non-parallel manner with respect to the axes of the second and third electrically conductive elements.

11. The method of claim 10, further comprising providing the second and third electrosurgical devices with sharpened distal tips configured for percutaneous tissue penetration.

12. The method of claim 10, further comprising operatively coupling a potentiometer to at least one of the first, second, and third electrosurgical devices.

13. The method of claim 10, further comprising operatively coupling an activation switch to the first electrosurgical device.

14. The method of claim 10, wherein moving along the single resection line causes a degree of energy transmission to change.

15. The method according to claim 10, further comprising connecting the first and second electrosurgical devices in parallel.

16. The method according to claim 10, further comprising circulating a fluid through the third electrosurgical device.

17. The method according to claim 10, wherein the first electrosurgical device includes a blade, the second electrosurgical device includes at least one needle electrode, and the third electrosurgical device includes at least one hollow needle electrode assembly.

* * * * *